United States Patent [19]

Voss et al.

[11] Patent Number: 5,080,653
[45] Date of Patent: Jan. 14, 1992

[54] INFUSION PUMP WITH DUAL POSITION SYRINGE LOCATOR

[75] Inventors: Laveille Voss, Foster City; Clyde K. Nason, Valencia, both of Calif.

[73] Assignee: Pacesetter Infusion, Ltd., Sylmar, Calif.

[21] Appl. No.: 509,933

[22] Filed: Apr. 16, 1990

[51] Int. Cl.$^5$ .................................................. A61M 1/00
[52] U.S. Cl. ............................ 604/152; 128/DIG. 12; 604/154
[58] Field of Search ............... 604/131, 151, 152, 153, 604/154, 155; 128/DIG. 12

[56] References Cited

U.S. PATENT DOCUMENTS

| | | | |
|---|---|---|---|
| 4,468,221 | 8/1984 | Mayfield | 604/152 |
| 4,652,260 | 3/1987 | Fenton, Jr. et al. | 604/154 |
| 4,676,122 | 6/1987 | Szabo et al. | 604/154 |
| 4,685,903 | 8/1987 | Cable et al. | 604/154 |

FOREIGN PATENT DOCUMENTS

| | | | |
|---|---|---|---|
| 319276 | 6/1989 | European Pat. Off. | 604/151 |
| 8103545 | 12/1981 | World Int. Prop. O. | 604/131 |

Primary Examiner—Gene Mancene
Assistant Examiner—Michael Lynch
Attorney, Agent, or Firm—Leslie S. Miller; Stuart O. Lowry

[57] ABSTRACT

An improved infusion pump is provided for controlled delivery of medication from a syringe to a patient, wherein a pump housing includes a syringe chamber and associated lock members for receiving and supporting the syringe in one of two different positions. The syringe includes a medication-containing barrel connected to a luer fitting at a nose end thereof by a luer neck of reduced cross sectional size. In one position, the syringe seats into the chamber with the luer neck protruding through an outlet port of mating size and with the luer fitting disposed outside the housing, such that the housing defines a lock member engaged axially between the syringe barrel and luer fitting to secure the barrel against axial displacement. In another position, a retainer key is adapted for installation into the syringe chamber at a position spaced inboard from the outlet port and defines an alternative lock member for axially securing the syringe with the luer fitting disposed inside the housing. In either position, a syringe piston plunger is controllably advanced by the pump into the barrel to deliver medication from the nose end of the syringe for administration to a patient via the luer fitting and infusion tubing or the like connected thereto.

19 Claims, 3 Drawing Sheets

INFUSION PUMP WITH DUAL POSITION SYRINGE LOCATOR

BACKGROUND OF THE INVENTION

Field of the Invention

This invention relates generally to improvements in infusion pumps of the type used for controlled delivery of medication to a patient. More specifically, this invention relates to an improved infusion pump designed to receive and support a medication-containing syringe in one of two different selected positions.

Infusion pump devices and systems are relatively well known in the medical arts, for use in delivering or dispensing a prescribed medication such as insulin to a patient. In one form, such devices comprise a relatively compact pump housing adapted to receive a syringe carrying a prescribed medication for administration to a patient through infusion tubing and an associated catheter or the like. The infusion pump includes a small drive motor connected via a lead screw assembly for motor-driven advancement of a syringe piston plunger to administer the medication to the patient. Programmable control means are normally provided for operating the drive motor continuously or at periodic intervals to obtain a closely controlled and accurate delivery of medication over an extended time period. Such infusion pumps are utilized to administer insulin and other medications, with an exemplary pump construction being shown and described in U.S. Pat. Nos. 4,562,751 to Nason et al., 4,678,408 to Nason et al, and 4,685,903 to Cable et al. U.S. Pat. Nos. 4,562,751, 4,678,408, and 4,685,903 are hereby incorporated herein by reference.

Infusion pumps of the general type described above have provided significant advantages and benefits with respect to accurate delivery of medication over an extended time period. The infusion pump is often designed to be extremely compact and may thus be adapted to be carried by the patient, for example, by means of a belt clip or the like. As a result, important medication can be administered with precision and in an automated manner, without significant restriction on the patient's mobility or life-style.

To achieve accurate and reliable delivery of medication to the patient in response to motor-driven advancement of a syringe piston plunger, it is extremely important for the associated syringe barrel to be secured or locked in place within the pump housing. Otherwise, inadvertent displacement of the syringe barrel toward the piston plunger can result in undesired excess medication delivery. Conversely, inadvertent displacement of the syringe barrel away from the piston plunger can result in undesired nondelivery of medication upon subsequent advancement of the piston plunger.

More specifically, as shown in U.S. Pat. Nos. 4,562,751, 4,678,408, and 4,685,903, one relatively simple arrangement for securely locking the syringe barrel includes the formation of a narrow profile luer neck connected between the barrel and a luer fitting at a nose end of the syringe. This reduced profile neck is adapted to seat within a matingly sized outlet port defined by the pump housing, such that the housing at said outlet port provides an effective lock member engaged axially between the syringe barrel and luer fitting. As a result of this axial engagement, the syringe barrel is securely seated or locked relative to the pump housing.

However, this locking arrangement positions the luer fitting on the exterior of the pump housing where it effectively increases the overall size and length of the infusion pump. In an effort to reduce the pump length and size, some patients attempt to mount the syringe with the luer fitting recessed into the pump housing at the inboard side of the outlet port. Unfortunately, in this recessed position, the infusion pump lacks structural means for preventing undesired displacement of the syringe barrel toward the piston plunger. Such undesired displacement can occur due to inadvertent bumping of infusion set components, resulting in undesirable and uncontrolled delivery of a medication bolus to the patient.

There exists, therefore, a significant need for an improved infusion pump adapted for securely supporting the barrel of a medication-containing syringe in either one of two different mounting positions, thereby permitting a luer fitting at the nose end of the syringe to be positioned outside or alternately recessed into the pump housing. The present invention fulfills these needs and provides further related advantages.

SUMMARY OF THE INVENTION

In accordance with the invention, an improved infusion pump is provided for use with a medication-containing syringe to obtain precision controlled delivery of the medication through infusion tubing or the like to a patient. The improved infusion pump includes means for receiving and supporting the syringe in one of two different operating positions.

The infusion pump includes a pump housing having an elongated syringe chamber formed therein for receiving and supporting a medication-containing syringe barrel and associated piston plunger. A pump drive motor is operated by a programmable controller on a selected basis to dispense medication from the syringe. The drive motor includes a mechanical output such as a lead screw assembly connected to the piston plunger for controlled advancement of the plunger into the syringe barrel. The medication is dispensed from the syringe barrel through a luer neck of reduced cross sectional size at the nose end of the syringe, and further through a luer fitting adapted for connection to infusion tubing or the like.

In a first or normal mounting position, the syringe barrel and plunger are seated within the housing chamber to position the narrow profile luer neck within a matingly sized outlet port at one end of the chamber. Accordingly, the portions of the pump housing defining the outlet port protrude radially to a position disposed axially between the syringe barrel and the luer fitting, such that the housing provides a lock member securing the syringe barrel against fore-aft displacement with respect to the housing. In this position, the luer fitting is located at the exterior of the housing.

A second or alternative mounting position is obtained by installing a retainer key into the syringe chamber at a position spaced inboard from the outlet port. In the preferred form, the retainer key and housing include cooperating lock structures for securely fixing the retainer key to the housing in a selected position. The retainer key includes a second or alternative lock member fitting axially between the syringe barrel and the luer fitting when the syringe is placed into the chamber with the luer fitting at the inboard side of the outlet port. The retainer key thus locks the syringe barrel against axial fore-aft displacement with the luer fitting disposed at a recessed position within the pump housing.

Other features and advantages will become more apparent from the following detailed description, taken in conjunction with the accompanying drawings which illustrate by way of example, the principles of the invention.

DESCRIPTION OF THE DRAWINGS

These and other advantages of the present invention are best understood with reference to the drawings, in which.

DETAILED DESCRIPTION OF THE PREFERRED EMBODIMENT

Figure 1:
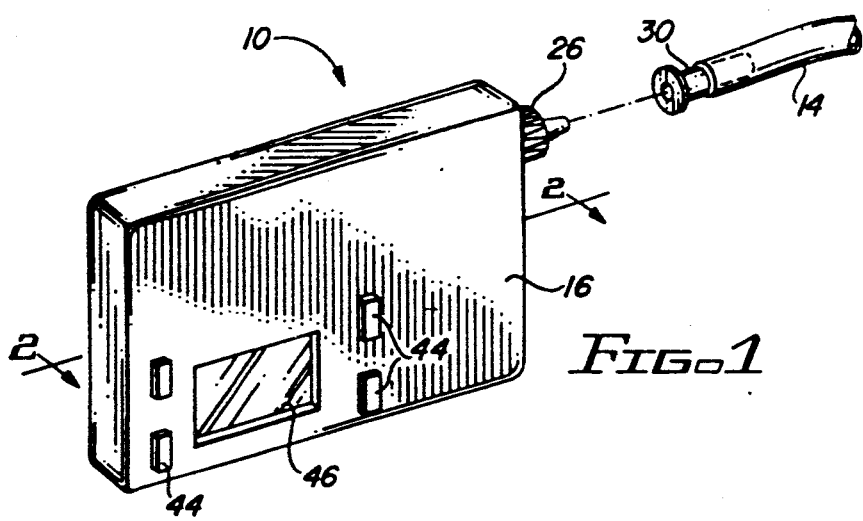
FIG. 1 is a front perspective view illustrating a medication infusion pump adapted for controlled delivery of medication to a patient, and further adapted for dual position mounting of a medication-containing syringe.
Figure 2:
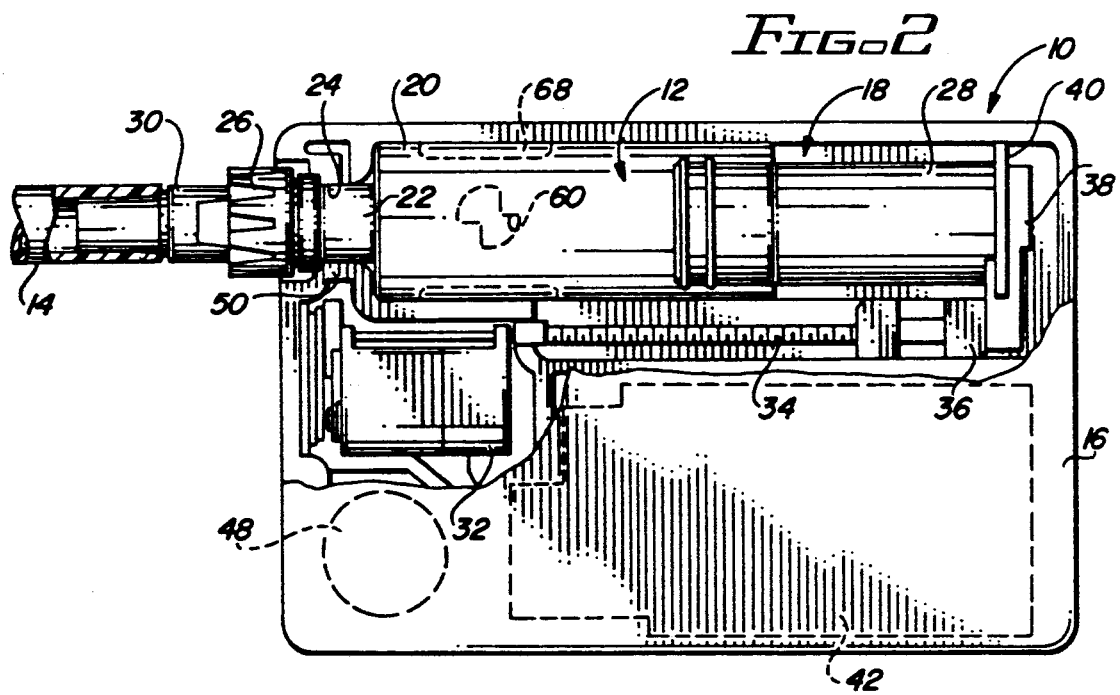
FIG. 2 is an enlarged rear elevational view of the infusion pump of FIG. 1, with portions broken away to illustrate pump operating components and further depicting a medication-containing syringe mounted in a first or normal position.
Figure 3:
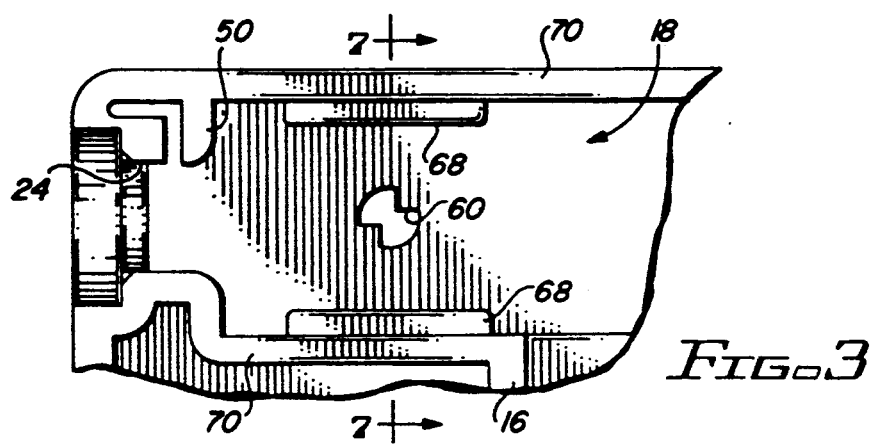
FIG. 3 is an enlarged fragmented rear elevational view corresponding generally with a portion of FIG. 2 with the syringe removed.
Figure 4:
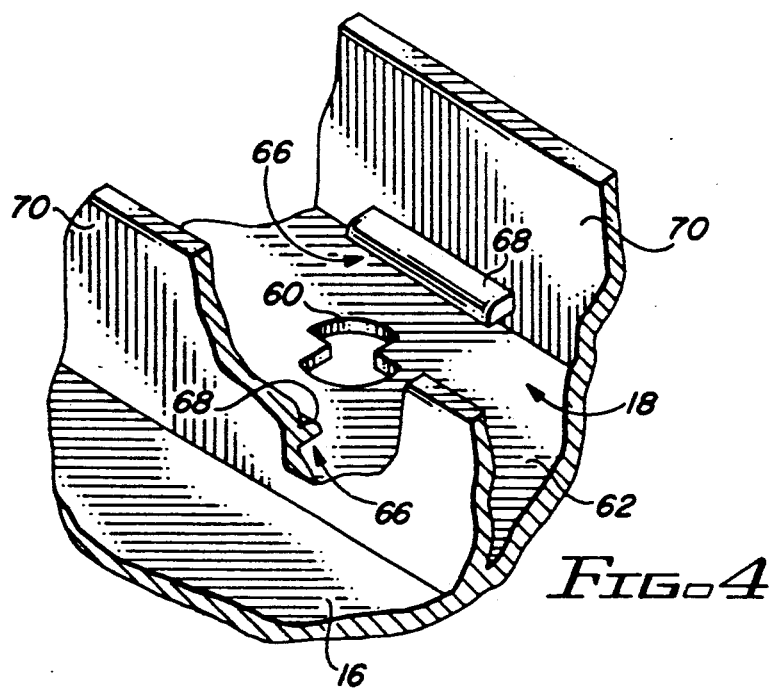
FIG. 4 is an enlarged fragmented perspective view illustrating further construction details of the syringe chamber depicted in FIG. 3.
Figure 5:
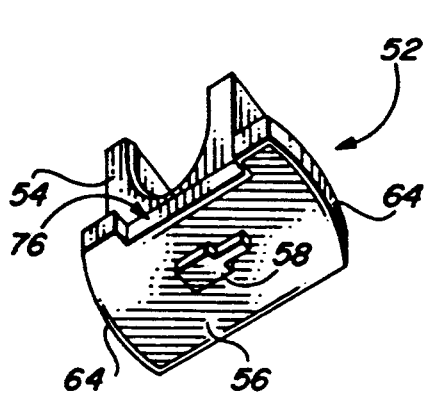
FIG. 5 is a perspective view illustrating one preferred form of a retainer key adapted for installation into the syringe chamber.
Figure 6:
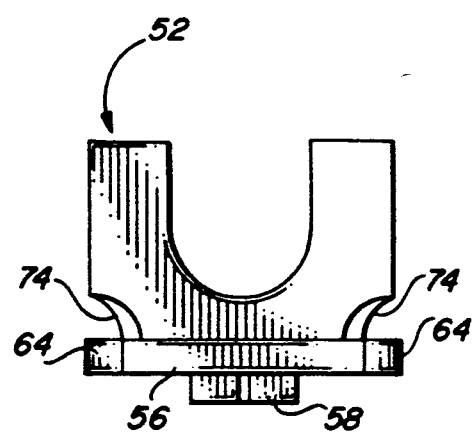
FIG. 6 is an enlarged side elevational view of the retainer key of FIG. 5.
Figure 7:
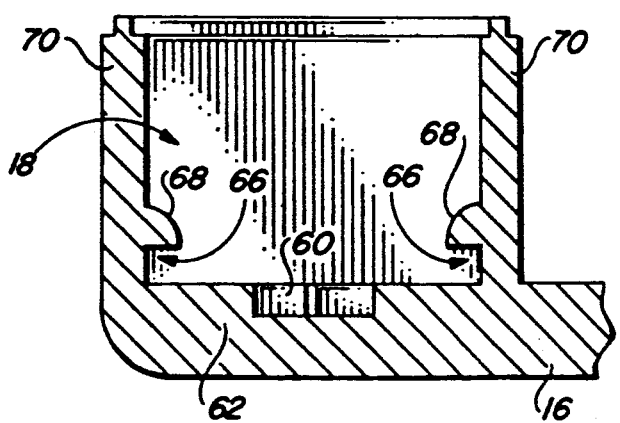
FIG. 7 is an enlarged fragmented vertical sectional view taken generally on the line 7—7 of FIG. 3.

As shown in the exemplary drawings, an infusion pump referred to generally in FIG. 1 by the reference numeral 10 is provided for controlled administration of medication to a patient. The infusion pump 10 receives and supports a medication-containing syringe 12 (FIG. 2), and includes means for automatically and programmably operating the syringe 12 to deliver the medication through infusion tubing 14 or the like to the patient. In accordance with the invention, the infusion pump 10 is adapted for mounting of the syringe 12 in a secure and stable manner in one of two different positions.

The infusion pump 10 has an overall construction and operation which is generally known in the art. More specifically, with reference to FIGS. 1 and 2, the infusion pump 10 includes a relatively compact pump housing 16 defining an elongated chamber 18 (FIG. 2) adapted to receive and support the syringe 12 charged with a selected medication, such as insulin, to be administered to a patient. This chamber 18 is shown in an open state in FIG. 2 although it will be understood that a removable access plate (not shown) forming a portion of the pump housing will be used to close the chamber 18 during normal operation of the infusion pump.

The medication-containing syringe includes a syringe barrel 20 joined at a nose end thereof to a luer neck 22 of reduced diametric size to seat snugly within an outlet port 24 formed in the pump housing 16. The luer neck 22 is joined in turn to a female luer fitting 26, with these components cooperating to support or lock the syringe barrel 20 in a first or normal position seated within the housing chamber 18, as will be described in more detail. A syringe piston plunger 28 extends from the aft end of the barrel 20 and may be advanced into the barrel to deliver the medication therefrom. In this regard, the medication is normally dispensed to the patient through the infusion tubing 14 or the like having an appropriate male luer fitting 30 engagable with the female luer fitting 26. The infusion tubing 14 is associated in turn with a catheter (not shown) or the like for transcutaneous infusion of the medication into the patient.

The infusion pump 10 further includes a compact drive motor 32 mounted within the housing 16 and coupled mechanically to the syringe piston plunger 28 for purposes of advancing the plunger in a precision controlled manner to dispense the medication. The illustrative drive motor 32 corresponds with the infusion pump depicted in U.S. Pat. Nos. 4,562,751, 4,678,408, and 4,685,903, which are incorporated by reference herein, although it will be understood that alternative drive motor mechanisms may be used, if desired. The illustrative drive motor 32 has a mechanical output adapted to rotate a lead screw 34 to translate a lead screw nut 36 having a fixture 38 thereon for engaging an enlarged flange 40 at the outboard end of the piston plunger 28.

A programmable controller 42 within the housing 16 can be set by the attending physician or other appropriate personnel by use of an array of buttons 44 (FIG. 1) with a corresponding display panel 46 on the front of the housing 16 providing appropriate information regarding set status and/or pump operation. As is known in the art, the controller 42 is adapted to couple a battery power supply 48 or the like to the drive motor to obtain a desired drive motor operation on a continuous or intermittent basis, in accordance with the controller program.

In accordance with the invention, the improved infusion pump 10 accommodates selective mounting of the medication-containing syringe 12 in either one of two different operating positions within the syringe chamber 18. In this regard, as viewed in FIG. 2, the syringe 12 can be installed in the first or normal operating position with the narrow profile luer neck 22 seated within the housing outlet port 24. In this position, the housing structure defining the outlet port provides an effective lock member 50 protruding radially inwardly to a position axially between the nose end of the syringe barrel 20 and the luer fitting 26.

Accordingly, the housing lock member 50 effectively secures or locks the syringe barrel 20 against fore-aft displacement relative to the syringe chamber 18, such that medication dispensing is precision controlled in response to relative advancement of the piston plunger 28. However, in this normal mounted position, the luer fitting 26 is located at the exterior of the pump housing 16. This exterior position of the luer fitting 26 provides a rigid protrusion effectively extending one end of the housing 16, and is sometimes considered to be undesirable by persons using the infusion pump.

Accordingly, the improved infusion pump 10 of the present invention accommodates an alternative mounting position for the syringe 12, wherein the luer fitting 26 is seated in a recessed position inside the housing 16. Importantly, when this alternative mounting position is used, alternative lock means are provided for securing the syringe barrel 12 against fore-aft displacement within the chamber 18.

More specifically, with reference to FIGS. 3-9, a retainer key 52 (FIGS. 5, 6, 8 and 9) is provided for installation into the syringe chamber 18 at a position spaced inboard from the outlet port 24. In general terms, this retainer key 52 and the pump housing 16 include interengageable lock structures designed for positive locked installation of the key at a predetermined inboard-spaced position relative to the outlet port. The retainer key 52 is shaped to mirror the geometry of the lock member 50 at the outlet port 24 and thereby permit seated reception therein of the reduced profile luer neck 22 for purposes of locking the syringe barrel against fore-aft displacement in the chamber. Importantly, the inboard spaced position of the key 52 is chosen to permit the female luer fitting 26 to seat axially between the retainer key 52 and the outlet port 24, such that the smaller male luer fitting 30 protrudes through the outlet port 24.

In the preferred form, the retainer key 52 is constructed from lightweight molded plastic or the like to include a generally U-shaped collar 54 protruding and opening upwardly from a base plate 56. A contoured locator key 58 is formed on the underside of the base plate 56 for reception into a contoured keyhole seat 60 recessed into a base wall 62 of the syringe chamber 18. Moreover, opposite end edges 64 of the base plate 56 are sized for relatively snug reception into undercut cavities 66 formed below a pair of lock ribs 68 which protrude inwardly toward each other from opposite side walls 70 (FIGS. 4 and 7) defining the chamber 18.

Figure 8:
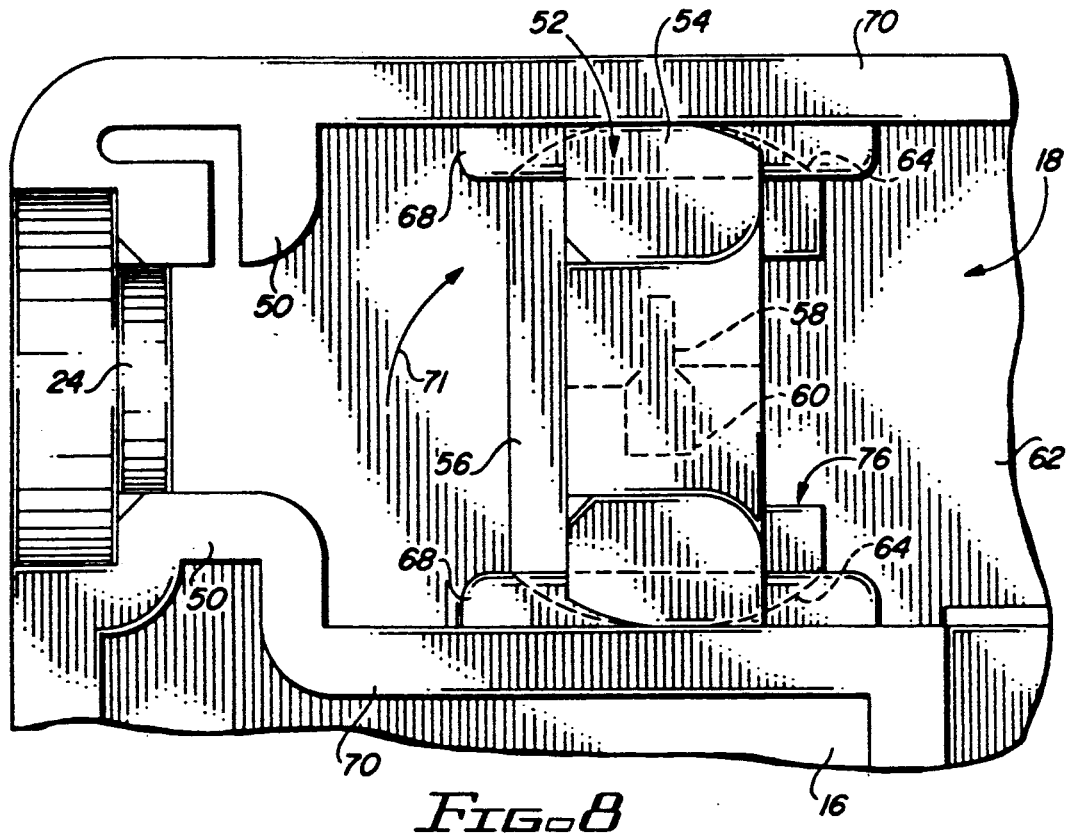
FIG. 8 is an enlarged fragmented rear elevational view generally corresponding with FIG. 3, but depicting the retainer key installed into the syringe chamber.

The retainer key 52 is inserted into syringe chamber 18 at an angle with the locator key 58 seated within the keyhole seat 60, and then turned in the direction of arrow 71 in FIG. 8 through an arc of about 45-60 degrees to extend transversely across the chamber 18. In this regard, while the contoured shapes of the locator key 58 and keyhole seat 60 may vary, the geometry of the keyhole seat 60 is relatively enlarged to accommodate rotation of the locator key therein as the base plate 56 is rotated to a position extending transversely across the chamber 18 as shown in FIG. 8.

Such rotation displaces the end edges 64 of the base plate 56 into the undercut cavities 66, and correspondingly carries the collar 54 to a tight, essentially snap-fit position seated between the chamber side walls 70. To facilitate this rotation, the end edges 64 are desirably convexly curved, and leading corner edges 72 of the collar arms are recessed. In addition, notches 74 at the lower edges of the collar (FIG. 6) permit reception therein of the lock rib 68 on the chamber side walls 70.

With the retainer key 58 locked in place, the syringe 12 can be installed quickly and easily into the syringe chamber with the luer neck 22 cradled within the lock collar 54. In this position, the female luer fitting 26 is interposed between the retainer key 52 and the inboard side of outlet port 24, thereby placing the luer fitting 26 in a recessed position inside the pump housing 16. The retainer key 52 is axially engaged between the luer fitting 26 and the nose end of the syringe barrel 20. In this regard, to facilitate unidirectional installation of the retainer key 52, one side edge 76 of the base plate 56 is conveniently recessed, as indicated by arrow 76 in FIG. 5, to receive the rounded edge of the syringe barrel 20 without interference.

Figure 9:
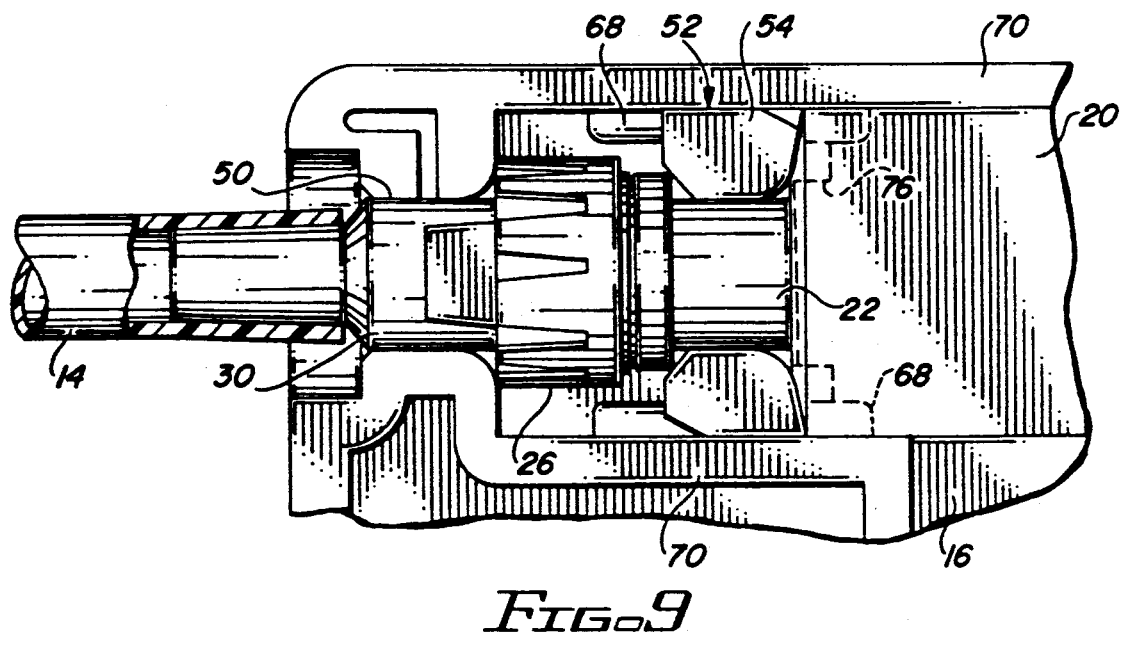
FIG. 9 is a fragmented rear elevational view similar to FIG. 8, but illustrating the medication-containing syringe mounted in a second or alternative position.

The infusion pump 10 of the present invention thus includes dual locator means for dual position mounting of a medication-containing syringe in a secure and stable manner. The syringe can be mounted with a luer fitting 26 positioned on the exterior of the pump housing (FIG. 2) or recessed into the interior of the pump housing (FIG. 9). In either position, the syringe barrel 20 is securely locked against fore-aft displacement, such that medication dispensing can be controlled in a precision manner by operation of the syringe piston plunger 28.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. In an infusion pump having a pump housing defining a syringe chamber adapted for receiving and supporting a syringe barrel with a piston plunger received therein, wherein the infusion pump includes first means for retaining the syringe barrel in a first position within the syringe chamber, the improvement comprising:
   second means for removable insertion into the syringe chamber for retaining the syringe barrel in a second position within the syringe chamber.

2. The combination of claim 1 wherein said second means and the pump housing include engageable lock means for securely mounting said second means within the syringe chamber.

3. The combination of claim 2 wherein said lock means securely and removably mounts said second means within the syringe chamber.

4. The combination of claim 1 wherein said second means comprises a generally U-shaped lock collar.

5. The combination of claim 4 wherein said pump housing includes a base wall joined between a pair of side walls cooperatively defining the syringe chamber, said side walls having a pair of lock ribs formed respectively thereon and projecting into the chamber generally toward each other, said lock ribs cooperating with said base wall to define a pair of undercut cavities, and further wherein said lock collar includes a base plate having outwardly projecting end edges for snug fit rotation into said undercut cavities.

6. The combination of claim 5 wherein said collar further includes notches formed therein for relatively snug fit reception of said lock ribs when said base plate end edges are received into said undercut cavities.

7. The combination of claim 5 wherein said base wall has a contoured keyhole seat formed therein, and further wherein said base plate includes a contoured locator key for reception into said keyhole seat, said locator key being rotatable within said keyhole seat to permit rotation of said collar to displace said base plate end edges into said undercut cavities.

8. The combination of claim 7, wherein said keyhole seat and said locator key comprise means for preventing overrotation of said locator key in said keyhole seat.

9. The combination of claim 1 wherein the syringe includes a luer neck of reduced cross sectional size between a nose end of the syringe barrel and a luer fitting, said pump housing defining an outlet port at one end of the syringe chamber, said first means being axially engageable between said barrel nose end and said luer fitting to retain the syringe barrel relative to the pump housing with the luer fitting disposed outside the pump housing.

10. The combination of claim 9 wherein said second means, when inserted into the syringe chamber, axially engages between said barrel nose end and said luer fitting to retain the syringe barrel relative to the pump housing with the luer fitting disposed inside the pump housing.

11. The combination of claim 1 wherein the syringe barrel is further retracted into the syringe chamber in its second position that in its first position.

12. The combination of claim 1 wherein axial movement of the syringe barrel in either direction is inhibited by the first means when the syringe barrel is in the first position, and by the second means when the syringe barrel is in the second position.

13. An infusion pump assembly, comprising:
   a syringe having a syringe barrel adapted to receive a selected medication, a piston plunger slidably received into an aft end of said barrel and adapted for advancement into said barrel to dispense the medication through a nose end of the barrel, a luer fitting, and a luer neck of reduced cross sectional size joined between said barrel nose end and said luer fitting;
   an infusion pump including a pump housing defining an elongated syringe chamber with an outlet port at one end thereof, said syringe being receivable into said chamber syringe in a first position with said luer neck seated within said outlet port such that a portion of said housing defining said outlet port extends into axial engagement between said barrel nose end and said luer fitting to retain said syringe in said first position with said luer fitting disposed at the exterior of said housing;
   a retainer key for insertion into said chamber at a position spaced inboard from said outlet port; and
   means for securing said retainer key within said chamber, said syringe being receivable into said chamber in a second position with said luer neck seated within said retainer key such that said retainer key extends into axial engagement between said barrel nose end and said luer fitting to retain said syringe in said second position with said luer fitting disposed within said chamber.

14. The infusion pump assembly of claim 13 wherein said pump further includes means for controllably advancing said piston plunger into said syringe barrel.

15. The infusion pump assembly of claim 13 wherein said retainer comprises a generally U-shaped lock collar having a shape generally corresponding to the shape of said portion of the housing at said outlet port.

16. The infusion pump assembly of claim 14 wherein said pump housing includes a base wall joined between a pair of side walls cooperatively defining the syringe chamber, said side walls having a pair of lock ribs formed respectively thereon and projecting into the chamber generally toward each other, said lock ribs cooperating with said base wall to define a pair of undercut cavities, and further wherein said lock collar includes a base plate having outwardly projecting end edges for snug fit rotation into said undercut cavities.

17. The infusion pump assembly of claim 16 wherein said collar further includes notches formed therein for relatively snug fit reception of said lock ribs when said base late end edges are received into said undercut cavities.

18. The infusion pump assembly of claim 16 wherein sid base wall has a contoured keyhole seat formed therein, and further wherein said base plate includes a contoured locator key for reception into said keyhole seat, said locator key being rotatable within said keyhole seat to permit rotation of said collar to displace said base plate end edges into said undercut cavities.

19. An infusion pump assembly, comprising:
   a syringe having a syringe barrel adapted to receive a selected medication, a piston plunger slidably received into an aft end of said barrel and adapted for advancement into said barrel to dispense the medication through a nose end of the barrel, a luer fitting, and a luer neck of reduced cross sectional size joined between said barrel nose end and said luer fitting; and
   an infusion pump including a pump housing defining an elongated syringe chamber with an outlet port at one end thereof, said housing defining first means axially engageable between said barrel nose end and said luer fitting for supporting said syringe barrel against axial displacement within the pump chamber, with said luer fitting disposed outside the pump housing;
   said pump having further including second means adapted for removable seated insertion into the pump chamber and being axially engageable between sid barrel nose end and said luer fitting for supporting said syringe barrel against axial displacement within the pump chamber with said luer fitting disposed inside the pump housing.

* * * * *